United States Patent [19]
Piso et al.

[11] Patent Number: 6,038,021
[45] Date of Patent: *Mar. 14, 2000

[54] OPTICALLY BASED ON-LINE FIBER MONITORING SYSTEM WITH DRIFT COMPENSATION

[75] Inventors: John S. Piso, Framington; Dennis K. Briefer, Marlborough, both of Mass.

[73] Assignee: Scientific Technologies, Inc., Fremont, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/988,809

[22] Filed: Dec. 11, 1997

[51] Int. Cl.$^7$ ..................................................... G01N 21/00
[52] U.S. Cl. .................. 356/238.2; 356/429; 250/559.01
[58] Field of Search ............................... 356/237.1, 238.1, 356/238.2, 238.3, 242.1, 239.5, 239.8, 429–431; 250/559.41, 559.01, 559.03, 559.15, 548, 559.4; 26/70; 73/159; 223/39; 324/61, 130; 378/54

[56] References Cited

U.S. PATENT DOCUMENTS

| | | | |
|---|---|---|---|
| 3,582,661 | 6/1971 | Pijls | 356/238.2 |
| 3,907,440 | 9/1975 | Eichenberger et al. | 356/238.2 |
| 4,208,625 | 6/1980 | Piso | 324/61 |
| 4,436,427 | 3/1984 | Schwartz | 356/238.2 |
| 4,812,043 | 3/1989 | Vanstaen | 356/238.2 |
| 5,099,504 | 3/1992 | Pettit | 378/54 |

*Primary Examiner*—Hoa Q. Pham
*Attorney, Agent, or Firm*—Flehr Hohbach Test Albritton & Herbert LLP

[57] ABSTRACT

Denier and other optically transmissivity-dependent parameters of yarn are monitored on-line and in real-time with a preferably microprocessor-controlled high frequency modulated-demodulated optically-based system. An LED is spaced-apart from an array of preferably identical photodetector ("PD") diodes that will track one another, with the yarn spaced between one of the PDs. The LED outputs preferably collimated light in response to a periodic LED drive signal, and yarn characteristics will affect light received by at least one PD in the array. An output signal from a first PD is fedback to the LED driver to continuously compensate the system against dust or other factors affect LED transmission and PD light reception. An output signal from a second PD is coupled to a fraction of the drive signal so as to enhance dynamic range. This signal is amplified and AC-coupled to a sample and hold that samples during a stable active portion of the LED drive signal to demodulate the relevant signal. The sampled and held magnitude is digitized and coupled to a CPU to provide measurement data as to denier and other characteristics of the yarn. The CPU controls operation of the system and can communicate bilaterally with a host computer. A third PD is used to self-calibrated the system.

36 Claims, 5 Drawing Sheets

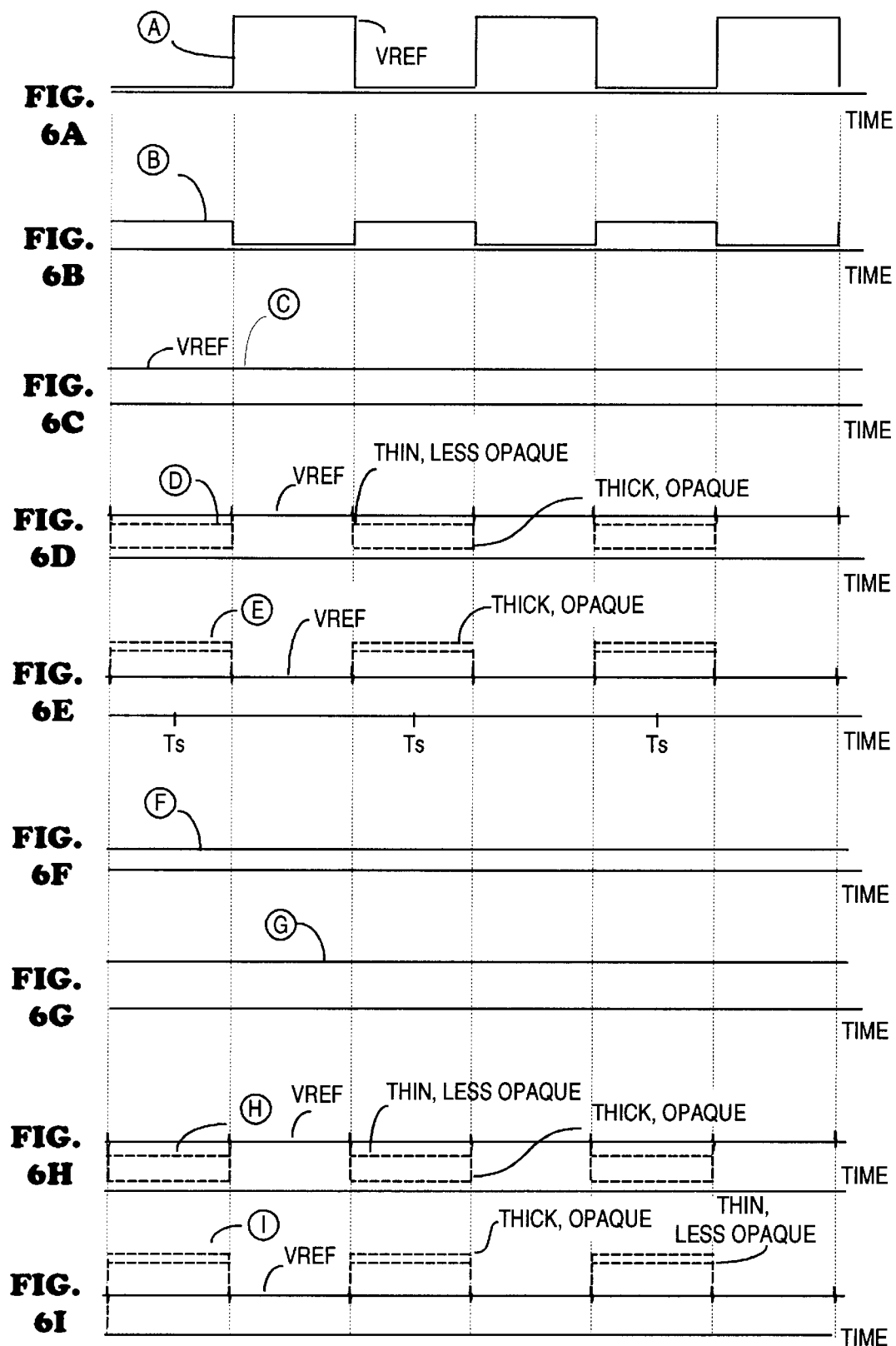

OPTICALLY BASED ON-LINE FIBER MONITORING SYSTEM WITH DRIFT COMPENSATION

FIELD OF THE INVENTION

This invention relates to methods and systems for continuously monitoring and measuring characteristics of a moving filament-like material or fiber, such as the denier of yarn (synthetic and/or natural), and more specifically to improving reliability of such measurements and providing additional quality control monitoring functions as well.

BACKGROUND OF THE INVENTION

As shown in FIG. 1, it is known in the art to provide an on-line system 10 that produces a yarn or filament 20 from a process system 30. Process system 30 typically may include a continuous polymerization process and/or an extrusion melt process. Included within system 30 in FIG. 1 can be pre-polymer pumps and a reactor pump and/or an additive injection system with an extrusion booster pump. The spinning process portion of system 30 will also include a plurality of planetary/series pumps, extrusion heads, spin-finish pumps and spinerettes. The multi-filaments 20-1 output by a spinerette are combined to make yarn 20, which will be understood to include multiple filaments. Yarn 20 is provided to an input spool 40, to be collected on a take-up spool 50, which rotates in the direction shown. Yarn 20 may be perhaps 0.004" in diameter, and it may comprise dozens or hundreds of multi-filaments 20-1.

Extruded yarn material 20 can be processed for a variety of applications ranging from manufacturing, home furnishings (e.g., carpets, upholstery, drapes), apparel, and industrial yarns, depending upon the fineness of the yarn. "Denier" is a commonly used unit of fineness for yarn, and is equivalent to 1 g weight per 9 Km length of material. It is important to control quality and characteristics of the extruded yarn, including its denier.

Historically, larger denier yarn (e.g., perhaps 1,200 denier for carpet material) was manufactured with interlace nodes 60, produced along the length of the extruded material at intervals of perhaps 1 cm to 20 cm. The nodes were formed by causing the yarn to enter an air jet associated with a yarn end at a velocity exceeding the yarn exit velocity. The resultant bunching-up on the jet input side created compacted regions or nodes whose spaced-apart distances were a function of process parameters, especially yarn speed (perhaps 3 Km/min) and air jet pressure. These nodes prevented larger denier filament from unravelling during subsequent process, especially in a dry or static-electricity environment. More recently, nodes are also produced during fabrication of apparel class yarns as well, e.g., finer yarn in the range of a 100 denier or so. In apparel class yarns, the nodes are spaced-apart perhaps 1.2 cm to 2.5 cm or so.

As depicted in FIG. 1, it is not uncommon for produced yarn to have undesired broken segments or frayed portions 70. If such material is used to manufacture fabric, the imperfections adversely affect color dyeing as well as material consistency, for example because imperfect dye sites are present. Unfortunately such broken or frayed or even segments with missing strands have been relatively difficult to detect in the past, with resultant loss in yield of acceptable yarn produced.

Variations in denier, as well as changes in viscosity and/or density, can also affect color dyeing and consistency of material produced from a large number (perhaps a thousand) of packages of filaments that, ideally, would have identical characteristics. For example, the ability to extrude synthetic yarn is influenced by the flowability or viscosity of the material. Thus, a change in viscosity can manifest itself with changes in the crystalline structure of the material itself, including for example reorientation of the chain molecules within the material.

Material produced from filaments that have poorly controlled denier consistency, or viscosity or density characteristics, or excessive frayed and broken strands, may have to be discarded. Understandably discarding such material is a waste of time and resources, and degrades the effective yield of filament production. Further, many yarns undergo secondary manufacturing processes, such as draw texturing. It is important that the secondarily-processed material also be of consistent quality.

Conventionally, prior art systems 10 have attempted to measure denier by passing the extruded filament through a slotted capacitive bridge measuring system 80. For example, U.S. Pat. No. 3,879,660 to Piso discloses the use of a slotted balanced four-leg bridge capacitive sensor head system 80, in which the filament passed between the two plates of one of the capacitors. The bulk of the filament contributed a measurable charge imbalance as the filament passed through a somewhat large, e.g., about 10 mm×10 mm, effective window in the capacitive bridge. The sensor head output signals were analog, and the data acquisition signal processing circuitry coupled to the sensor head output signals made and processed perhaps ten measurements per second. The essentially analog denier measuring system was sensitive to electrical drift, especially due to changes in ambient temperature. Capacitive measurement systems are highly influenced by moisture in the yarn or measurement environment, which can degrade measurement reliability. Thus, such prior art systems could not readily be used to measure natural fibers, e.g., cotton, wool, flax, due to their high moisture content. Further, the effective measurement window was too large to sense frayed or broken strands 70, and no attempt was made to attempt to monitor nodes 60 in large denier filaments.

The '660 Piso system provided absolute denier measurements relative to a zero datum point that was obtained as a measurement with no filament present. The system provided calibration compensation such that the filament measurement output in the absence of any filament was forced to be zero denier. Unfortunately, contaminants from various sources could build-up between the capacitor plates, with the result that system 80 would eventually report too large a denier (due to bulk from contaminants) for a given filament size. The effective denier of the contaminants was perhaps 5 to 10, which meant that contamination drift could easily render apparel filament measurements grossly erroneous within a few days.

In addition, the system tended to exhibit signal drift and loss of absolute accuracy with respect to measured denier. Cleaning the sensor head to remove contaminants to restore signal accuracy meant taking the filament producing system off-line, perhaps every day or so. Although periodic sensor head cleaning improved measurement fidelity, production yield was reduced due to cleaning down-time, and quality of the material produced could suffer, prior to cleaning. At best, the '660 system could provide accurate measurements of denier, providing the analog system was maintained contaminant free and ambient temperature was controlled. No attempt to made to measure filament characteristics other than denier.

U.S. Pat. No. 4,208,625 to Piso disclosed an improved capacitive denier measuring system 80 with automatic calibration to compensate for sensor head drift. In addition to providing automatic zero compensation as in the '660 system, the 625 system provided automatic gain compensation gain. In essence, thermal gain drift was compensated by altering capacitive bridge excitation by a reference amount, and dynamically adjusting the system to produce a known corresponding change in the bridge output signal. Such gain compensation was done periodically, e.g., hourly, daily, or as frequently as seemed appropriate. (To further minimize thermal effects, the sensor head was maintained at about 50° C.)

The normal filament-present measurement signal developed by the capacitive sensor head was combined with compensating signals representing zero gain and actual gain. The resultant automatic gain calibration meant that periodic system shutdowns for sensor head cleaning were not needed as often. While the '625 system represented improved denier measurement performance, this system was still analog in nature, and limited to about 10 measurements per second. As with the earlier system, the only filament characteristic measured was absolute denier. As a result, even if accurate denier measurements could be maintained for a period exceeding a few days, the resultant filament might still contain frayed or broken strands, viscosity changes, density changes, color changes, among other characteristic changes. However, even perfectly sized yarn that contained such changes could still result in a finished woven material that was defective, and would have to be rejected.

A somewhat different approach to denier-type measurement is disclosed in U.S.Pat. No. 5,099,504 (1992) to Pettit. Pettit '504 sensed yarn thickness by monitoring output from a particle radiation source, wherein the yarn to be measured was disposed between the source and an appropriate detector unit. While Pettit's device could provide a measure of denier and even density (providing the volume of the yarn was known), the device did not make meaningful use of optical properties of the yarn. Pettit's system does not respond to dye site defects, which can cause dying imperfections during fabrication with the yarn. Further, Pettit's device was expensive to fabricate (probably at least $1,000), cumbersome (probably at least 1 ft$^3$) and exhibited some defects described earlier herein that characterize prior art approaches to denier and related yarn measurements.

In general, prior art systems have not been able to achieve DC stability better than 1 part per 1,000 to perhaps 1 part per 10,000. This DC stability parameter essentially affects measurement resolution, before any system drift occurs. Systems conventionally operate from perhaps 10V power supplies, and DC drift has limited Denier reading to perhaps 1% accuracy. Further, overall gain in prior art systems has been limited to perhaps 20,000 or less.

Prior art attempts to optically measure denier have long been plagued with the adverse effects of ambient conditions, including ambient light. For example, the room in which measurements are made will typically be illuminated with lights that will have a 60 Hz flicker component. This 60 Hz ambient light modulation will degrade optically based systems, and must somehow be accounted for.

In short, analog capacitive type denier measuring systems leave much to be desired, especially when fine apparel class yarns are to be monitored. Voltage gains in the prior art systems described typically was less than 5,000 or so, and signal to noise ratio did not permit greater than about 1 mV/denier. Capacitive based systems are also too susceptible to moisture, which can degrade measurement reliability. Particle radiation-based systems also leave much to be desired. Basically, prior art systems are blind to potential defects in the yarn or filaments being examined. Such defects include frayed, broken, or missing strands, changes in optical characteristics (e.g., viscosity, color, density). Other characteristic changes that could result in materials produced with the filaments being rejected after fabrication went similarly undetected in the prior art.

Thus there is a need for a rapidly executing high gain filament monitoring system that can measure absolute denier, denier spreads and variability, as well as monitor other filament parameters that affect quality control of the filament at the spinning level and/or the texturing level of production. Without limitation, such parameters should include optical characteristics, viscosity and density characteristics, interlace characteristics as well as dye sites and related structural changes that affect optical quality of the finished yarn. The system should operate on-line to detect defects including frayed or broken strands, missing or extra filaments, filament pump malfunction including jet contamination.

Such system should include automatic compensation for zero-denier and for gain, and feedback compensation for changes in the measurement medium. Further, such a system should enable on-line real-time monitoring of quality control production of the filament or yarn being produced and measurement results should not be substantially degraded by the presence of moisture. Preferably such measurements should be accurate within at least about ±1% and in applications ranging from spinning, spin drawing, spin draw texturing, draw texturing, and air jet texturing. The system should provide high but stable gain, low susceptibility to ambient lighting effects, and preferably should provide a resolution of perhaps 0.1 denier. Further, the system should provide a signal/noise ratio exceeding at least 20,000:1, and a sensitivity of at least 100 mV/denier.

The monitoring system should be substantially maintenance free, and be relative immune to the effects of contaminants and thermal drift. The monitoring system should not require frequent downtime of the yarn production system for maintenance. Finally, the system should be relatively inexpensive, uncomplicated to operate, and should be self-contained within a small package.

The present invention provides such a system.

SUMMARY OF THE INVENTION

The present invention measures denier and other parameters for filament-like material such as yarn (synthetic and/or natural, or even wire) in real-time with an on-line balanced optically-based system using transmissivity related characteristics. Unlike prior art capacitive systems, the optically based system is not highly susceptible to moisture and thus can be used to monitor natural fibers, and because it uses high frequency sampled modulation-demodulation, the system is not affected by 60 Hz ambient light effects.

The optical sense system includes an array of photodiodes ("PDs") fabricated on a single silicon chip that can receive light emitted by a light emitting diode ("LED") source and focused upon a small effective window through which the yarn passes. The LED is driven by a microprocessor controlled pulse train drive signal that has an LED-active time period and an LED-inactive time period. The LED may output visible and/or IR or laser-frequency light to enable different transmissivity-related measurements to be made on yarn.

During measurement, the yarn passes between the LED and at least two PDs and will absorb (or scatter) at least some of the transmitted light. Thus, the PD-received light intensity contains information as to yarn bulk (e.g., denier), and optical qualities including yarn color, density, viscosity, presence of dye site and material defects. Resolution and the small effective window size permit the system to recognize the presence of broken or frayed or missing strands, among other defects.

Within the common array, the various PDs will experience like drift and thus will track closely together. One PD in the array is a reference PD that is disposed outside the field of view that is affected by the presence or absence of yarn. This reference PD receives pulsed light energy from the LED and feeds back an analog pulsed signal (in synchronism to the drive signal) to the LED driver. This optically completed feedback circuit ensures that a constant intensity maximum LED output is received, even if dust, LED or PD ageing or the like affect detection of transmitted light. If variations do affect the amount of light received by the reference PD, the feedback automatically and continuously will vary the LED drive signal amplitude to compensate as required. So compensated, the present invention can output zero value to represent zero denier.

A second, measurement, PD is in the field of view affected by the yarn. This measurement PD outputs pulses in synchronism with the active drive signal. The measurement pulses are summed with a portion of the drive signal to increase dynamic range, by cancelling the drive component from the measurement PD-provided pulses. Under microprocessor control, the measurement PD signals are periodically sampled, preferably during the middle portion of the active period of the drive signal. The sampled signals are then held and digitized, and the digitized measurement PD data are coupled to the microprocessor.

Perhaps once an hour the present invention enters a calibrate mode for a few seconds during which any corrections to compensate for drift in signal gain and the like are computed and made. To facilitate calibration, a third, calibration, PD is also disposed within the field of view affected by the yarn. Similarly to the measurement PD, the pulsed output of the calibration PD is summed with a portion of the drive signal to increase dynamic range.

In calibration mode yarn is first removed from the field of view by a solenoid under microprocessor control. With no yarn, the measurement PD should output a zero offset signal of known magnitude. The yarn is returned to the system and a new measurement PD value is produced, from which the zero offset signal is microprocessor-subtracted. Next a calibration switch is energized such that the calibration PD output is now summed with a constant weighting factor to the measurement PD output signal. The summed signal is sampled, held and digitized and after offset correction, the summed signal is microprocessor-checked to ascertain whether weighting increased the measurement PD signal by the known given weighting factor. If the increase is other than this amount (e.g., components have drifted, gain has varied), the microprocessor calculates a new internal calibration factor that is then applied to all data until the next calibration mode occurs. After calibration, the calibration switch is again left open and measurement PD data of yarn is sampled, held, digitized and weighted as necessary with the new calibration factor.

The microprocessor-stored data may be output to an external device that can readout denier, density, or other characteristics. Alternatively, the microprocessor may be coupled to a host computer than inputs desired denier, tolerance, and other system parameters to the present invention. The present invention can then control the yarn manufacturing process, e.g., by varying pump speed, temperature, tension, time, etc. to force the yarn under manufacture to conform to the host computer input values.

LED driving and signal processing occur synchronously, and AC-coupled high gain amplified PD signal magnitudes are sampled during a center portion of the sampled waveform. Because the system operates to modulate and demodulate signals at high frequency, low frequency 60 Hz ambient light effects are not seen. In summation, the present invention automatically compensates for variations in light absorption between LED and PDs, and can operate longer before it is necessary to turn off the fabrication process system to permit sensor cleaning. The invention provides auto-zero closed loop compensation to ensure zero denier output data in the absence of yarn. The invention further provides an automatic calibration auto-gain feature to ensure that a known yarn will produce an expected denier output signal, despite drift in system components and gain. These compensation signals are generated continuously. The auto-gain compensation is generated anew whenever yarn is removed or reinserted into the system field of view window.

Other features and advantages of the invention will appear from the following description in which the preferred embodiments have been set forth in detail, in conjunction with the accompanying drawings.

BRIEF DESCRIPTION OF THE DRAWINGS

FIGS. 6A–6I depict node waveforms indicated in the system of FIG. 5.

DETAILED DESCRIPTION OF THE PREFERRED EMBODIMENT

Figure 1:
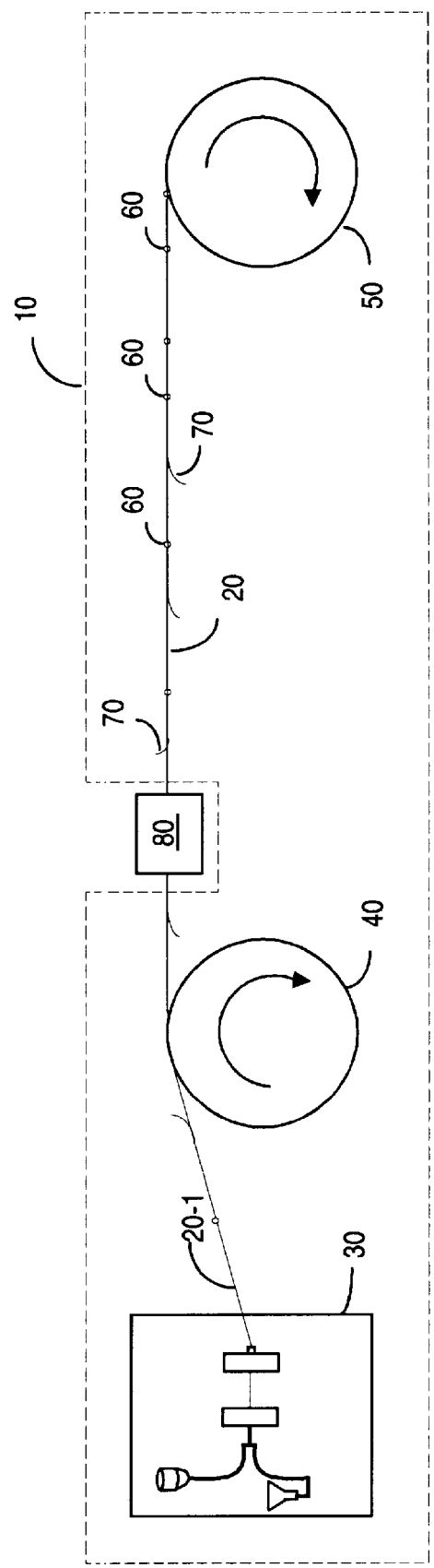
FIG. 1 depicts generally filament production and denier monitoring using an on-line capacitive sensor system, according to the prior art.
Figure 2:
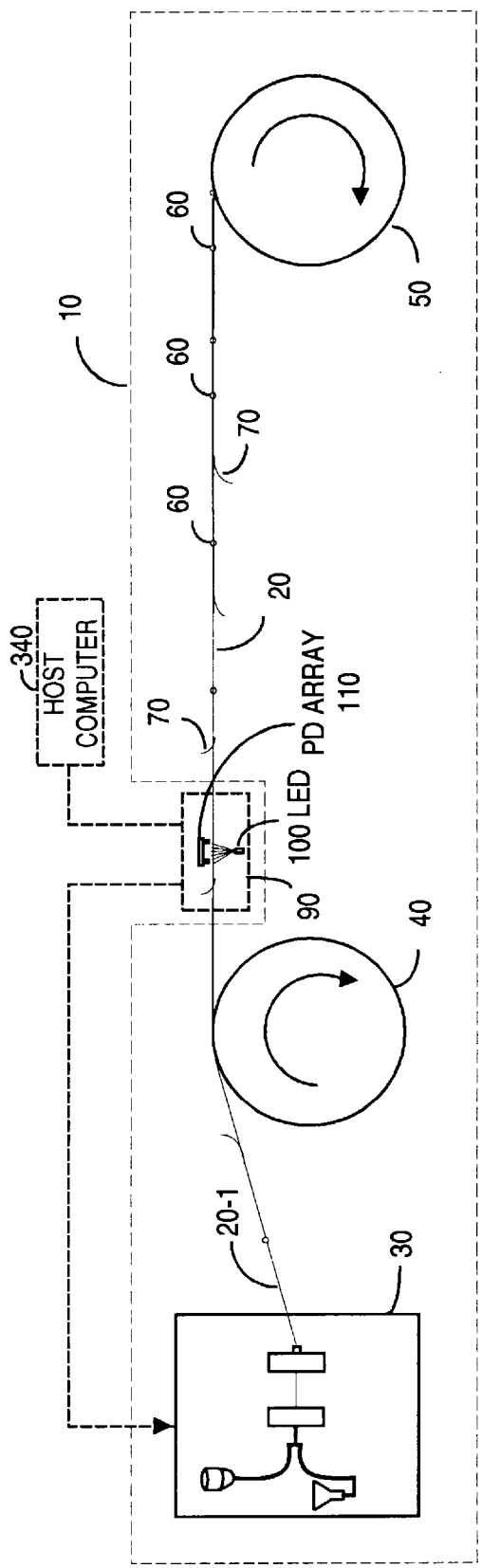
FIG. 2 depicts generally filament production and denier monitoring using an on-line optical sensor system, according to the present invention.

With reference to FIG. 2, the present invention provides an optically based closed-loop sampling measurement system 90 that may be used with conventional yarn producing systems 10. Reference element numbers in FIG. 2 or the other figures herein that are identical to those in FIG. 1 may refer to substantially identical system elements. Thus, it is to be understood that system 90, according to the present invention, may be used to measure denier and other characteristics of yarn, regardless of how the yarn is fabricated. Further, because the present invention can function without susceptibility to moisture, it will be understood that reference herein to a filament-like material or to yarn or to yarn 20 may include not only synthetic yarn, but natural fiber yarn (e.g., cotton, flax, wool, among others), as well as combinations of synthetic and natural materials. It will be further appreciated from FIG. 2 that system 90 is used on-line, e.g., in real-time during fabrication of yarn 20.

As indicated by FIG. 2, the present invention may be used to control the yarn manufacturing process, e.g., to feedback signals that may vary process parameters such as temperature, time durations, tensions, chemical quantity, etc. to ensure that the quality of yarn 20 as monitored by system 90 is acceptable. Further, the present invention may be coupled to a host computer that can download process parameters into system 90, essentially dictating what measurable values of quality, e.g., denier, and what tolerance values are acceptable.

In addition to various signal processing circuitry, system 90 includes a light emitting diode ("LED") 100 spaced-part from an array 110 of preferably at least three light receiving photodiodes ("PDs"). Normally yarn 20 will pass between LED 100 and PD array 110. Yarn 20 thus normally blocks detection by one or more PDs in array 110 of some of the light emission from LED 100. By signal processing the array-received light, the thickness and/or optical characteristic(s) of yarn 20 may be learned. Circuitry within system 90 provides the signal processing, as well as automatic zero denier feedback, and automatic gain calibration to maintain stability of system 90.

Figure 3:
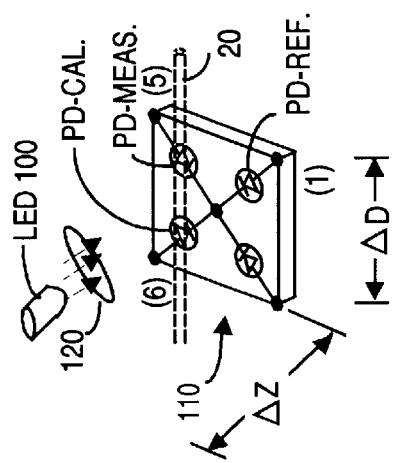
FIG. 3 is a perspective view of an LED, lens, and array of photodiode detectors, according to a preferred embodiment of the present invention.

FIG. 3 is a perspective view of a commercially available quad photodetector array 110 that is spaced-apart a distance ΔZ of about 0.1" (2.5 mm) from LED 100. As shown, yarn 20 passes between LED 100 and PD array 110, such that at least one PD within array 110 will detect some of the light emitted by LED 100 and not absorbed or scattered by yarn 20. Quad diode array 110 may be a 5980 integrated circuit ("IC"), commercially available from Hamamatsu Co. of Japan. The array is essentially square, with anode ends of the various diodes being spaced-apart about 0.03" (0.75 mm) on a side, with all diodes formed on a common IC substrate. The cathode ends of the four diodes are coupled together, as shown in FIG. 3. Array 110 advantageously can detect radiation from a device 100 that emits visible light, infrared, or even laser light. Because the PDs are all fabricated on a common substrate within array 110, outputs from each PD will be substantially identical, and ageing and related changes will affect all the PDs similarly. Thus, PD output signals will closely track each other over time.

In the preferred embodiment, LED 100 is a 4 mm diameter 100 mW dissipation device that is operated with moderate current levels (e.g., 4 mA to 10 mA) and emits red light of about 660 nm. Alternatively, LED 100 may be a 400 nW dissipation device operated at similar current levels that emits infrared radiation of perhaps 800 nm. In some applications it may be desirable to make LED 100 a laser diode that operates at perhaps 50 mA current. A laser diode would be very effective for very small denier yarn, e.g., perhaps 10 denier. As noted, however, the preferred PD array 110 can detect light from any of these emitting devices 100.

Preferably device 100 includes its own high quality lens such that PD array 110 sees a substantially uniform light intensity. If desired, however, a collimating lens 120 may be used to focus and/or filter pulses of radiation emitted by LED 100. Lens/filter 120 is disposed between LED 100 and a transparent glass window that protects array 110 while admitting light into the array. Whether a discrete lens 120 is used or not, the collimated light intensity from LED 100 should define a preferably small (e.g., perhaps 4 mm$^2$ or less) effective optical window through which yarn 20 passes.

The yarn absorbs (and/or scatters) at least some of the LED 100 emitted radiation. As described herein, PD-array detected light enables the present invention to discern information as to the optical density and optical mass or size of yarn 20.

Within array 110 only three of the four PDs are presently used: reference PD 110-1 (or "REF-PD" or "PD-REF"), measurement PD 110-2 ("MEAS.-PD" or "PD-MEAS"), and calibration PD ("CAL-PD" or "PD-CAL") 110-3. Of course other PD detectors and PD configurations may instead be used. As seen from FIG. 3, the reference PD (PD-REF) is disposed out of the effective field of optical view, such that the presence or absence of yarn 20 will not affect how much light OD-REF receives from LED 100.

Mechanically, the LEDs, collimating lens, and receiving photo-diode array form a balanced optical system having inherent stability. As will be described, the optical measurement and monitoring system is disposed to compensate for measurement signal drift arising from variations in the optical sensor components.

Figure 4:
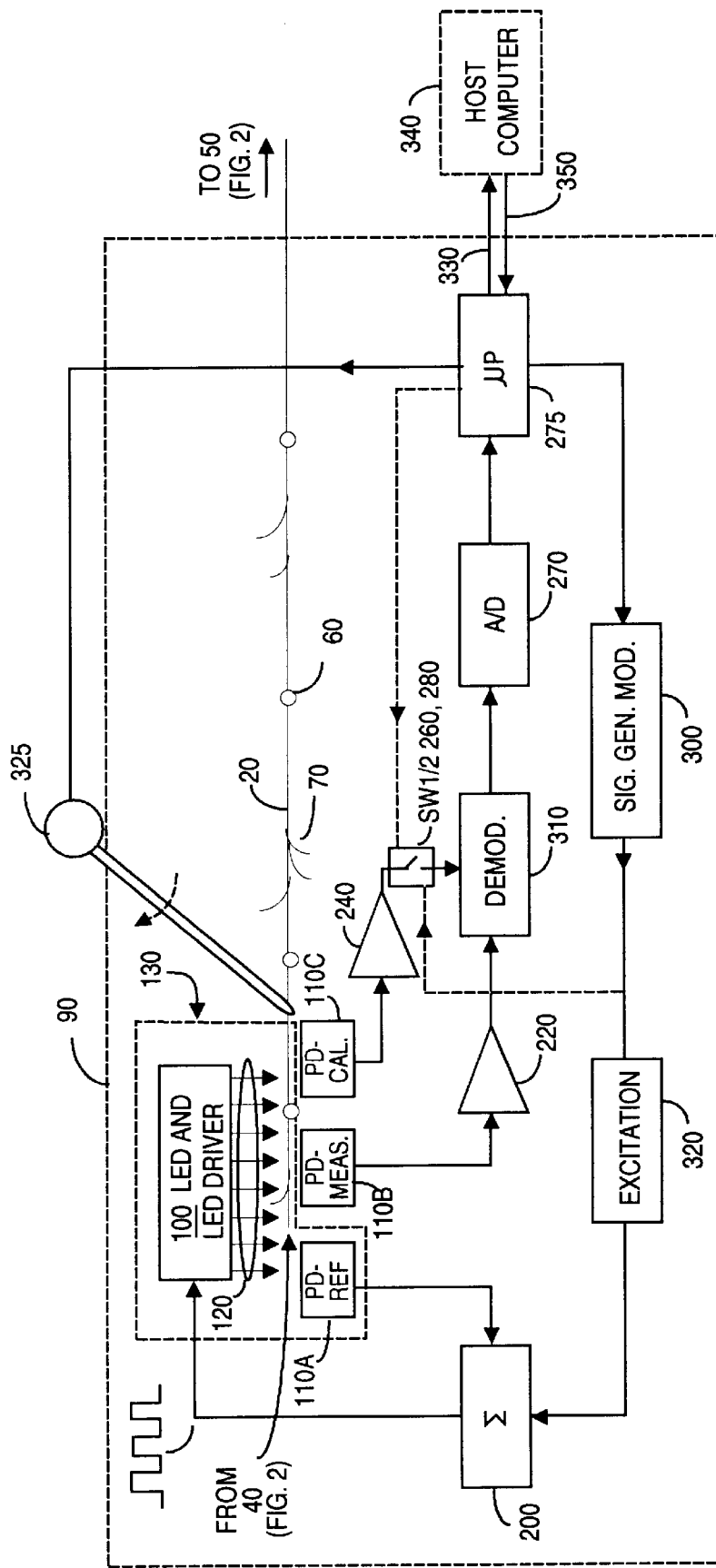
FIG. 4 is a block diagram of an optical sensor system, according to the present invention.
Figure 5:
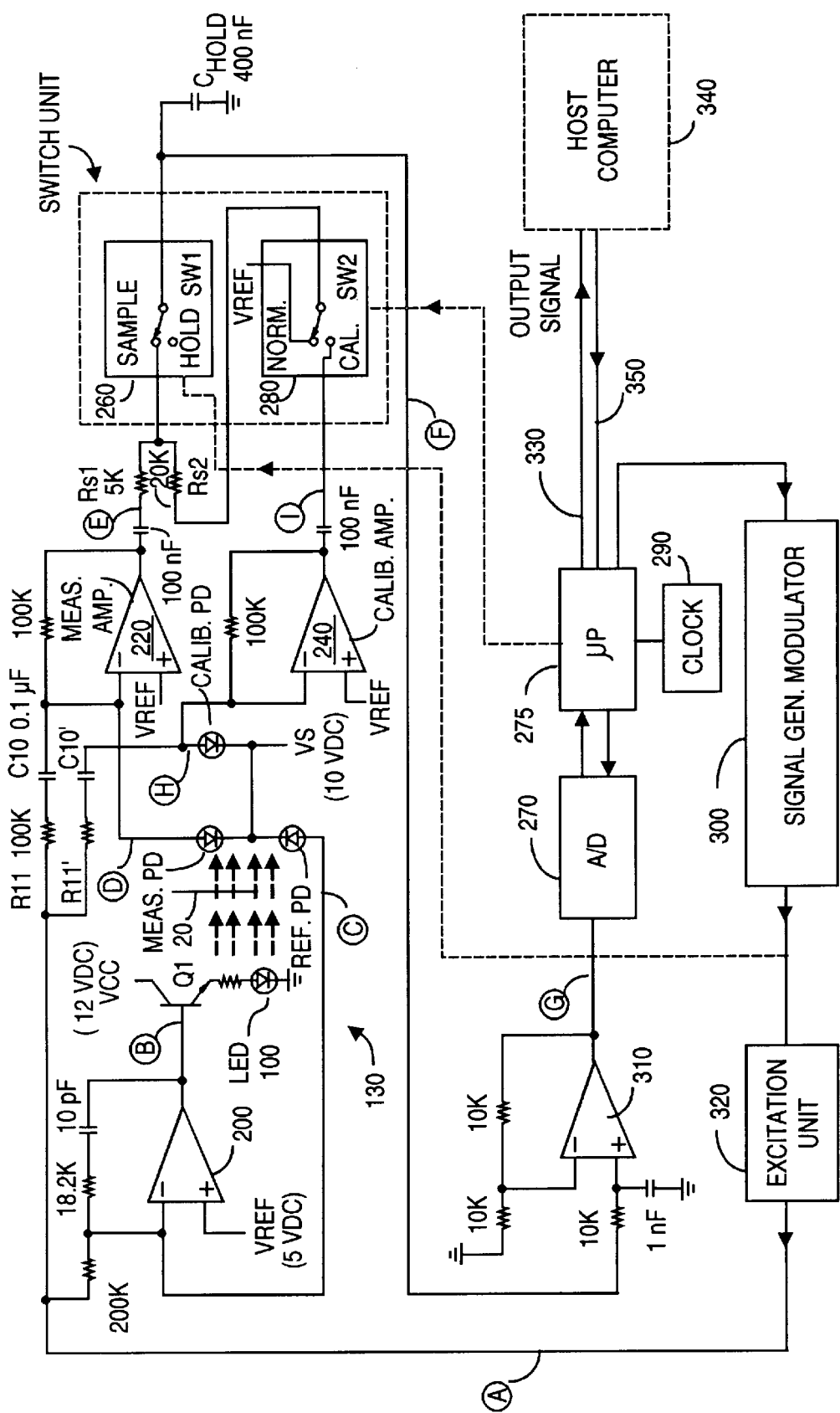
FIG. 5 is a simplified schematic diagram of an optical sensor system, according to the present invention.

FIG. 4 is a block diagram of an optically based measurement system 90, according to the present invention, while FIG. 5 is a simplified schematic diagram of system 90. As indicated in FIG. 4, LED 100 emits light that may fall on each of the PDs used in the present invention. However, because of its physical location, REF-PD 110-A is out of the effective field of view such that the amount of light it detects is independent of whether yarn 20 is or is not in the field of view window of system 90.

In FIG. 5, block 130 denotes an optically closed analog feedback circuit used in the present invention to automatically compensate system 90 for the presence of dirt, component aging, etc. that can affect the amount of light received by array 110 from LED 100. Optical feedback block 130 can continuously and automatically compensate for dust on the optical glass window associated with array 110, for example, without having to take fabrication system 10 off-line to clean system 90.

A preferably 20 KHz pulse train with preferably 50% duty cycle 5V peak-peak drive signal A is input to block 130. This signal is inverted by amplifier 200 and the amplifier output signal (waveform B) drives the base of LED-driving transistor Q1. (Waveform A is shown in FIG. 6A, waveform B in FIG. 6B, waveform C is FIG. 6C, etc.) LED 100 is in the emitter of Q1 and when the LED drive signal A is active (low state), base signal B is high, and LED 100 conducts current and emits light. Regardless of whether yarn 20 is in the field of view, REF-PD 110A will detect light from LED 100, and feed the detected light signal (waveform C, see FIG. 6C) back to amplifier 200. The non-inverting input of amplifier 200 is coupled to a precise VREF potential, preferably 5.0V, which is obtained from a +12V power source from which system 90 operates. Amplifier 200 thus combines a scaled version of waveform A with REF-PD output waveform C, and adds VREF to this sum, and outputs waveform B as the amplified difference. Waveform C will be held by amplifier 200 to the VREF magnitude, about 5V.

In the preferred embodiment, amplifier 200 (and indeed all of the amplifiers shown in FIG. 5) is a JFET-input device exhibiting very high input impedance with a leakage current of perhaps 1–10 pA, and a gain bandwidth product of perhaps 16 MHz to ensure outputting signals with fast rise and fall transition times. Stability of amplifier 200 need not exceed perhaps 100 $\mu V/°$ C. as the amplifier is essentially AC-coupled, but with a DC-optically closed feedback loop.

When system 90 is manufactured, the signal from REF-PD is used to adjust Q1 emitter drive current such that with a clean obstruction-free optical system (e.g., no dust, etc.) the signal output from REF-PD will have a predetermined magnitude, e.g., VREF or 5V. This manufacturing adjustment may be used to ensure that in the absence of yarn 20, a zero denier data value will be output by system 90. The factory adjustment may be made using a potentiometer, although those skilled in the art will appreciate that adjustment of Q1 emitter current may be accomplished using other techniques. Of course other voltage magnitudes and LED driver configurations could be used.

Thereafter, when system 90 is actually used to monitor and/or quality control yarn production, optically-completed feedback 130 from REF-PD to amplifier 200 to LED 100 operates to compensate system 90 for smoke, dust, etc. that otherwise would reduce efficiency of the effective optical window. For example, if dust were present on LED 100, on the array 110 window, and/or on lens 120, output signal C from REF-PD would diminish. However the inversion provided by amplifier 200 would increase the magnitude of signal B, which would increase Q1 emitter current forcing LED to output more light, until the pretermined signal amount were again attained. By contrast, prior art systems would have to take fabrication system 10 off-line to clean the denier monitoring apparatus, as no continuous self-correcting feedback loop similar to loop 135 was provided.

Referring to FIG. 6A, waveform A preferably is a 20 KHz square-wave signal, in which system 90 is active when waveform A is low, during which 25 µs period LED 100 is emitting light. In the preferred embodiment, waveform A varies from 0V (low) to a high signal as large as VREF (5V). Of course other drive signal amplitudes, frequencies, and duty cycles could instead be used. Waveform B will be an inverted, reduced amplitude version of waveform A. Waveform C will be forced by feedback 130 to be approximately VREF, e.g., the same potential coupled to the non-inverting input of amplifier 200.

Unlike PD-REF, the presence or absence of yarn 20 from the optical path will affect the amount of light energy detected by PD-MEAS, see waveform D (FIG. 6D), and detected by calibration photodiode PD-CAL. 110C, waveform E (see FIG. 6E). Consider first the action of PD-MEASURE (110B).

With no yarn 20 present in the measurement window, PD-MEAS receives a maximum amount of light from LED 100 and will attempt to output a square-wave that is 180° out of phase with waveform A. If yarn were now introduced into the optical window, the magnitude of the square-wave would change, increasing for a dark, thick yarn. However to increase dynamic range of measurement amplifier 220, a fraction or portion of waveform A is coupled through resistor R11, capacitor C10 to node D. Essentially, the effective value of R11 is factory-adjusted during manufacture of system 90. This adjustment is made with no yarn in the measurement window to null-out the square-wave component of waveform D in the absence of any yarn 20. The resultant waveform D, shown in FIG. 6D, is at steady-state a flat trace of amplitude VREF with "glitches" corresponding to transition times of waveform A.

However, with yarn introduced, the positive-most portion of waveform D will decrease from VREF. For an opaque thick yarn, waveform D may decrease during the active portion of waveform A by a few hundred microvolts or so. This few hundred microvolt change results from measurement photodiode current going into the summing node of amplifier 220.

The measurement node D signal is then amplified by measurement amplifier 220 to produce waveform E, which waveform will increase from VREF by perhaps 5V for a thick, opaque yarn. When waveform A is inactive (high), waveform D will be about VREF, but during the active portion of waveform A, waveform D will modulate in height by up to several volts, according to the density and/or mass or size of yarn 20. These modulations are shown in phantom lines. Waveform E will also include transient glitches corresponding to waveform A transition times.

Although waveforms E are drawn as perfect pulses, in reality there will be finite waveform transition times. Waveform E is AC-coupled through scaling resistor Rs1 to the input of a first switch (SW1) 260. It will be appreciated that AC-coupling signals avoids the problems and limitations normally associated with DC amplifier drift.

Although the amplitude of waveform E is proportional to the optical qualities of yarn 20, it is important to examine waveform E at a time when the waveform has settled and is free of transition time influences. Thus, SW1 samples waveform E in essentially the middle of the active time, e.g., about 12.5 µs into the active period, where waveform A has a frequency of about 20 KHz. This sampling time is denoted Ts in FIG. 6E. SW1 opens and closes in response to a timing signal output by signal generator modulator 300. In the preferred embodiment, signal generator modulator unit 300 is implemented with programmable logic, although other implementations could of course be used.

The above-described Ts high frequency sampling promotes measurement accuracy and also effectively reduces any effect ambient 60 Hz lighting might have upon the various PDs in array 110. As a result, the present invention is substantially immune to the effects of 60 Hz ambient lighting, in contrast to prior art optically-based systems.

Accordingly, SW1 samples waveform E at times Ts every 50 µs. Under control of signal generator modulator 300, SW1 switches into the sample position for a duration of about 2 µs, and then switches into the hold position, permitting capacitor Chold (waveform F) to store the clean amplitude value that is sampled. In the preferred embodiment, Chold is about 400 nF. Waveform F will be a DC level corresponding to the sampled magnitude of waveform E.

Waveform F, a DC voltage of perhaps 4V, is coupled to amplifier 310, amplified, and resultant DC voltage I (perhaps 8V magnitude) is input to an analog-to-digital converter ("A/D") 270. Because amplifier 310 is DC-coupled, it is preferred that it have better voltage drift characteristics than the other amplifiers shown in FIG. 5, perhaps 1–5 µV/° C. The other characteristics of amplifier 310 may be identical to the other amplifiers.

Upon receipt of a conversion pulse controlled by microprocessor ("µP") 275, the digitized equivalent of voltage I is coupled to the microprocessor. Preferably the A/D conversion pulse occurs a few µs after completion of the perhaps 2 µs wide sampling pulse. Of course, other timing configurations, sample rates and sample durations could instead be used. It will be appreciated that the digitized data value coupled to µP 275 represents the optical density and/or mass of yarn 20.

Microprocessor 275 is preferably an 8-bit CMOS EPROM/ROM microcontroller IC, for example a commercially available Microchip PIC17C4X operating at about 16 MHz. The 16 MHz clock frequency is generated by a clock unit 290. Among other tasks, µP 275 divides the 16 MHz clock down to 800 KHz, which 800 KHz clock is then coupled to signal generator modulator 300. In turn, signal generator modulator further divides the clock frequency down to about 20 KHz, which is coupled to excitation unit 320 in which the basic waveform A signal is produced. Clock and pulse generator circuits to provide such timing signals are known in the art, and details are not given here.

The digital data value coupled to µP 275 may be output via a line 330 to a host computer 340, preferably at least an 80486-class computer. If desired, the digital data value may be used to control one or more parameters governing fabrication of yarn 20. For example, if the data value indicates the denier is too large, the data value may be coupled to yarn production system 10 to slightly speed-up the rate of production to somewhat thin down the diameter of the yarn. On the other hand, computer 340 may download data via line 350 to $\mu P$ 275, communicating to system 90 what denier, what denier tolerance, what integration time, etc. should be used to monitor yarn production. Line 330 and/or line 350 may be part of a standard computer input/output interface, e.g., an RS-232 interface.

Referring still to FIG. 5, $\mu P$ 275 controls a signal generator modulator 300 that in turn controls an excitation unit 320 that outputs the preferably 20 KHz square-wave signal A. As noted, excitation unit 320 is preferably implemented using a portion of a CMOS switch IC.

What has been thus far described functions extremely well. However, it is possible that drift in one or more components can vary the gain of system 90, to the detriment of the system accuracy. Accordingly, the present invention includes a calibration mode during which $\mu P$ 275 checks the gain of system 90, calculates and stores a new internal calibration value, if needed. The calibration mode typically lasts a few seconds and preferably is entered once an hour or so.

As will now be described, CALIB-PD, calibration amplifier 240, and second switch 275 play important roles in the calibration mode. Calibration mode is entered periodically, perhaps once per hour, and entry into this mode is preferably controlled by $\mu P$ 275, perhaps in response to a command from host computer 340. Alternatively, calibration mode is preferably entered when system 90 is turned on for the day, or whenever yarn 20 is removed from the optical window for whatever reason. (Removal of yarn 20 from the region between LED 100 and PD array 110 may be sensed in many ways that will be apparent to those skilled in the relevant art.)

In calibration mode, a zero offset measurement is first made with yarn 20 removed from the optical window, preferably by a solenoid controlled arm 325 (see FIG. 4), commanded by $\mu P$ 275. This preliminary zero offset measurement essentially informs the microprocessor as to the amount of offset produced by environmental conditions including drift. These zero signals are averaged for perhaps one second and are accepted by the microprocessor as representing the present offset zero level value. The yarn is now put back into the field of view, and of course the output from MEAS-PD will change. The microprocessor receives the new yarn-present value and subtracts therefrom the offset zero level value that was determined shortly before. The result of this subtraction represents the mass of the yarn being measured.

For a given yarn production the microprocessor knows, e.g., perhaps from data downloading from the host computer, what the desired denier should presently be. If the denier data just measured differs from the target data, the microprocessor computes and stores a scale correction factor. Of course since the yarn being produced may indeed be out of specification, the above-described correction is a relative correction.

In practice, the yarn manufacturer at this time will actually weigh 90 meters of the produced yarn to learn the true denier. If the weighed denier value differs from the target denier value, the yarn manufacturer will change microprocessor calibration settings, e.g., in the host computer, which can then down load new calibration settings for the microprocessor. Some 90 meters of yarn (or substantially more) is again produced and weighed until it is determined that the present invention is causing yarn fabrication system 10 to produce yarn of the correct denier. It is understood that microprocessor scale factors can cause system 90 to output actual (rather than relative) denier data, e.g., data indicating denier 100 when the denier is 100. The microprocessor scale factors resulting in correct denier yarn will in practice be good for perhaps 30 days, after which time drift in yarn fabrication system 10 will require new settings.

Alternatively, rather than produce and weigh yarn to determine initial microprocessor scale settings, yarn 20 can be removed and solenoid arm 325 can insert into the field of view a calibrated specimen. The calibrated specimen can be wire, perhaps painted black to minimized light scatter. Preferably such wire specimen will have a precisely known diameter and may be inserted and retracted from the field of view with the aid of magnetism. However in practice, it is common in the industry to actually weigh produced yarn to confirm denier.

The role of switch 2 (280) will now be described. Assume that microprocessor now holds good calibration or scale coefficient data to cause production of yarn that meets the denier target. After any subsequent re-zeroing, switch 2 (280) will be closed for an integration time of perhaps a few seconds, which time is typically commanded by host computer 340. It will be appreciated that hitherto switch 2 has not been closed and the calibration amplifier output signal G has not been used.

With yarn 20 in the system (perhaps returned by solenoid 325), and switch 2 in the CAL position, it is evident from FIG. 5 that the REF-PD and the CAL-PD should both output identical signals in response to detecting light output from LED 100. In the same manner that resistor-capacitor R11-C10 provided a null control for measurement amplifier 220, resistor-capacitor R11'-C10' are factory-adjusted (like, R11-C10, a one-time adjustment) to perform a similar null function for calibration amplifier 240. Again, the goal is to maximize the dynamic range of amplifier 240, whose output (waveform I) may increase from VREF by perhaps 5V for a thick, opaque yarn. Thus, waveform H (from CAL-PD) will be identical to waveform D (from MEAS-PD), e.g., excursions of up to a few hundred microvolts from VREF.

In a perfect system 90, waveform I would be identical to waveform E. However it is more reasonable to assume that component values within system 90 may have drifted, essentially changes in the various photodetectors as the remainder of the system is essentially AC-coupled. But photodetector drift can cause gain drift within the system over time. Thus, system 90 drift can be recognized by comparing magnitudes of waveform E and waveform I.

When SW 2 is in the CAL position, waveform I is AC-coupled through the CAL switch to resistor Rs2. The result is that waveform I will be added to waveform E, according to the ratio of resistors Rs1 and Rs2. In the preferred embodiment, these resistors are scaled so that in calibration mode, waveform I will increase waveform E by precisely 20%. In practice, switches 260 and 280, and indeed excitation unit 320, are all implemented from a single CMOS switch IC, e.g., an HC 4053 unit.

In normal fashion, switch one (260) continues to sample the combined waveform signal, which sample is then held by capacitor Chold to form a calibration mode signal F. This signal F is amplified by amplifier 310, digitized by A/D 270 and presented to $\mu P$ 270. Microprocessor 270 knows precisely what digital value will represent a 20% addition to waveform E. If the calibration mode signal F differs from what μP 270 expects, the μP will calculate and store a new microprocessor calibration factor. The microprocessor now ends calibration mode, SW 2 opens and remains open until a subsequent calibration mode is entered, and normal yarn measurements are resumed. The thus resumed normal measurements will henceforth be corrected by the new microprocessor calibration factor. This calibration factor will continue to be used until perhaps one hour later when the zero mode calibration process is repeated and perhaps a new calibration factor will be determined.

In this fashion, system 90 periodically recalibrates itself, performing an automatic gain correction. The result is that data provided by system 90 will be highly reliable, and indeed the integrity of the system will be renewed many times a day.

The AC-coupled high gain-bandwidth amplifiers used in the present invention, as well as the dynamic range increasing techniques described, permit the invention to achieve an overall gain of perhaps 100,000 from the PD outputs to the microprocessor input. This performance is accompanied by a DC stability of perhaps 1 part in 50,000, which permits denier measurements good to 0.1 denier. This performance is at least ten times better than prior art systems. Further, because of the synchronous manner in which signals are generated and processed, and because of the time-sampling that permits acquiring the best portion of a signal, the present invention can achieve excellent signal/noise ratios approaching perhaps 50,000:1, which is at least ten-fold better than prior art systems can achieve. As a result, the present invention can achieve from 1 mV to perhaps 200 mV per denier sensitivity, which is at least a ten-fold improvement over the prior art.

Although the present invention has been described with respect to using three photodiodes in an array, the fourth (or indeed still additional) photodiodes in array 110 could also be used. For example, the fourth photodiode in applicant's quad array could be used to sense stray strands. It may also be desirable to provide one or more emitting devices 100 that can output different frequency spectra. Emission at one wavelength may be desirable to determine denier, while emission at another wavelength, perhaps from a different emitter device 100, may be more useful to detect dye site imperfections.

It will be appreciated that the present invention may used to quality control material other than yarn, wire for example. In practice the present invention can accurately measure diameter, including wire diameter, to within about 0.000040". Further, the present invention may also be used to monitor material that is other than filament-like in shape, plastic film for example, as optical characteristic(s) of such material may be analyzed with system 90. Although the present invention has been described with respect to outputting digital data, if desired a denier readout device, perhaps a voltmeter, could be coupled to the analog output signal I, or a suitably interfaced digital readout device could be coupled to the microprocessor.

To summarize, the use of a well collimated light source that radiates to a nearby planar IC array of identical PDs that track one another, and the use of an optically closed loop 130 permits the present invention to automatically and continuously self-compensate for variables that could affect the transmission of light from LED 100 to the uniform reception of light by the various PDs. The use of AC-coupled amplifiers and a synchronous high frequency modulated-demodulated system that samples steady-state data promotes very high gain, excellent dynamic range, excellent signal-to-noise, and immunity to low frequency ambient light effects. Indeed, not only is the overall gain of the present invention approximately 100,000 but signal/noise ratios can approach 50,000. The present invention provides a high frequency response of about 10 KHz to 20 KHz (contrasted with perhaps 0.1 KHz for prior art systems). This high frequency response promotes fast transition times and permits sampling perhaps five times per 200 μs interval. Indeed, the high frequency response promotes interlace node analysis and defect counting.

Preferably microprocessor 275 stores as firmware a fast Fourier transform ("FFT") routine that enables a frequency analysis to recognize and utilize node count in monitoring the quality and characteristics of yarn. Other firmware within the microprocessor, or routines downloadable into the microprocessor, can facilitate other analysis techniques.

It will be appreciated that the present invention provides zero compensation and calibration compensation, to promote measurement reliability and accuracy. As noted, DC stability, signal/noise, overall gain, and denier/mV sensitive are each substantially better than what is achieved with prior art techniques. The present invention is indeed sensitive and stable enough and has sufficient resolution to analyze the structure of material, including without limitation dye site defects. er, and is essentially digital in nature. Whereas the prior art systems operated at relatively low sample rates (e.g., 10 samples/sec.), the present invention can operate up to 100 KHz or so, and can obtain at least 20,000 samples per second. Further, drift compensation in the present invention is substantially better than in such prior art measuring systems. In addition, the substantially smaller effective optical window provided by the present invention promotes finer granularity in resolving yarn (synthetic and/or natural) defects than was possible in the prior art. The ability of the present invention to discern transmissivity characteristics rather than pure mass or even shadow characteristics provides a very useful analytical tool. For example, density changes that might go undetected by a detection system that examined the effective shadow (e.g., thickness) of the yarn are readily detected by the present invention.

As noted, it may be useful in some installations to monitor different optical wavelengths. For example, if the yarn is polymer, IR transmissivity can provide useful data, as black components of IR pass through polymers, whereas visible light components are absorbed. For such materials, the microprocessor can be caused to compare ratios such as transmitted/scattered light to obtain density change information.

Some yarn may be produced with an absolutely uniform and correct denier, yet have dye color variations that should cause the yarn to be flagged as representing poor quality control. The weaving of material from many such yarns can unfortunately result in a finished material that exhibits unacceptable color changes or color dye streaks due to the dye variations. While prior art systems do not respond to such variations, the transmissivity detection provided by the present invention does so respond. Thus, system 90 can output data advising yarn producing system 10 and/or host computer 340 that although the presently produced yarn has proper denier, density or color variations are present that bear immediate quality control investigation.

As noted, in addition to providing denier information per se, PD array 110 can discern yarn optical characteristics such as data relating to viscosity, density, as well as color change of the yarn. Because system 90 operates sufficiently rapidly, yarn interlace or compaction characteristics are discernible from the periodic occurrences of the nodes. In all, the present invention can monitor these and other characteristics rapidly, continuously and in real-time and function not merely as a denier tester, but as a meaningful quality control device as well. Excluding the host computer, system 90 can be produced for under $200 and can be constructed to fit within a form factor of about 0.5"×3"×3" (1.2 cm×7.5 cm ×7.5 cm).

Modifications and variations may be made to the disclosed embodiments without departing from the subject and spirit of the invention as defined by the following claims.

What is claimed is:

1. An on-line system for real-time monitoring at least one characteristic of a material selected from a group consisting of (i) denier, (ii) density, (iii) viscosity, (iv) crystalline structure, (v) dye site, (vi) color, (vii) color variation, and (viii) interlace node occurrence, the system comprising:

a light source that emits collimated light synchronously in response to a drive signal;

a planar array that includes at least a first light detector and an identical second light detector, said array being closely spaced apart from said source permitting said material to pass therebetween such that at least a fraction of light received by said second light detector has passed through said material; and a synchronously optically coupled feedback circuit, having an input coupled to receive from one of said light detectors a signal synchronized in phase and frequency to said drive signal, said feedback circuit outputting said drive signal to said light source;

wherein an output signal from said second light detector is used to monitor said at least one characteristic of said material.

2. The system of claim 1, wherein said first light detector is disposed to receive light emitted by said light source regardless of whether said material is present.

3. The system of claim 1, wherein said light source is selected from a group consisting of (a) a diode emitting visible light, (b) a diode emitting infrared, and (c) a laser diode.

4. The system of claim 1, wherein said material is a filament-like material selected from a group consisting of (a) synthetic yarn, (b) natural material yarn, and (c) yarn including synthetic and natural material.

5. The system of claim 1, wherein:

said drive signal is a pulse train; and further including:

a first circuit so coupling a fraction of said drive signal to an output of said second light detector as to enhance dynamic range of said system.

6. The system of claim 5, wherein:

said array includes a third light detector identical to said second light detector, said third light detector disposed to receive less light from said light source when said material is present;

and further including:

a second circuit so coupling a fraction of said drive signal to an output of said third light detector so as to enhance dynamic range of said system;

a timing circuit that generates said drive signal, said driving signal having a duty cycle defining an active time region during which said light source emits light, and having an inactive time region;

a calibration mode switch having a switch input coupled to said output of said third light detector and having a switch output coupled to said switch input when said system is in a calibration mode, said switch output floating when said system is not in said calibration mode; and a sample and hold circuit, having an input AC-coupled an output of said second light detector and AC-coupled to said switch output;

said sample and hold circuit coupled to said signal proportional to an output of said second light detector when said system is not in said calibration mode, and coupled to said signal proportional to an output of said second light detector and coupled to a signal proportional to an output of said third light detector during said calibration mode;

wherein when said system is not in said calibration mode, a held signal at an output of said sample and hold switch has an analog amplitude proportional to at least one said optical transmissivity characteristic of said material; and when said system is in said calibration mode, said held signal has an amplitude augmented by said signal proportional to an output of said third light detector;

wherein a comparison between said held signal when said calibration mode switch is open and when said calibration switch is closed provides information enabling said system to be corrected for system drift.

7. The system of claim 6, wherein:

said timing circuit also generates, in synchronism with a mid-time portion of said active time region, a pulse train controlling said sample and hold circuit such that said sample and hold samples and holds a signal that is substantially free of transients associated with said drive signal.

8. The system of claim 6, further including:

an analog-to-digital converter having an input coupled to said output of said sample and hold circuit and having an output representing a digitized value of said sample and held output; and a microprocessor, having an input coupled to receive said output of said analog-to-digital converter, and having an output coupled to control said timing circuit.

9. The system of claim 6, further including:

a first AC-coupled amplifier coupled in series between said output of said second light detector and said input of said sample and hold circuit; and a second AC-coupled amplifier, identical to said first amplifier, coupled in series between said output of said third light detector and said input of said sample and hold circuit.

10. The system of claim 1, further including:

a sample and hold circuit, having an input AC-coupled to receive a signal proportional to an output of said second light detector; and a timing circuit that generates said drive signal, said driving signal having a duty cycle defining an active time region during which said light source emits light, and having an inactive time region;

said timing circuit also generating, in synchronism with a mid-time portion of said active time region, a pulse train controlling said sample and hold circuit such that said sample and hold samples and holds said signal proportional to an output of said second light source when said signal is substantially free of transients associated with said drive signal;

wherein an output of said sample and hold circuit has an analog amplitude proportional to at least one said optical transmissivity characteristic of said material.

11. The system of claim 10, further including:

an analog-to-digital converter having an input coupled to said output of said sample and hold circuit and having an output representing a digitized value of said sample and held output; and a microprocessor, having an input coupled to receive said output of said analog-to-digital converter, and having an output coupled to control said timing circuit.

12. The system of claim 11, wherein said microprocessor further includes an interface coupled to communicate with a host computer able to download data to said microprocessor to control said system.

13. The system of claim 11, wherein said microprocessor further includes an interface coupled to a manufacturing system that is fabricating said material, wherein said system controls said manufacturing system.

14. The system of claim 1, wherein said drive signal has at least one characteristic selected form a group consisting of (a) said drive signal is a periodic pulse train, (b) said drive signal has a duty cycle of about 50%, (c) said drive signal has a repetition rate ranging from about 10 KHz to about 100 KHz, and (d) said drive signal has a peak amplitude of about 5V.

15. An on-line system for real-time monitoring at least one characteristic of a material selected from a group consisting of (i) denier, (ii) density, (iii) viscosity, (iv) crystalline structure, (v) dye site. (vi) color, (vii) color variation, and (viii) interlace node occurrence, the system comprising:

a light emitting diode (LED) that emits collimated light synchronously in response to a drive signal having a duty cycle defining an active time region during which said LED emits light, and having an inactive time region;

a planar array of photodetectors that includes a reference photodiode (REF-PD), an identical measurement photodiode (MEAS-PD) and an identical calibration photodiode (CAL-PD), said REF-PD being disposed to receive light emitted by said LED regardless of whether said material is present, said CAL-PD being disposed to receive less light from said LED when said material is present;

said array being closely spaced apart from said source permitting said material to pass therebetween such that at least a fraction of light received by said MEAS-PD has passed through said material;

a synchronously optically coupled feedback circuit, having an input coupled to receive an output of said REF-PD comprising a signal synchronized in phase and frequency to said drive signal, and having an output providing said drive signal to said LED;

a sample and hold circuit, having an input AC-coupled to receive a signal proportional to said output of said MEAS-PD and AC-coupled, in a calibration mode, to receive a signal proportional to said output of said CAL-PD;

a timing circuit that generates said drive signal and further generates, in synchronism with a mid-time portion of said active time region, a pulse train controlling said sample and hold circuit such that a signal at the input of said sample and held is sampled and held at a time when said signal is substantially free of drive signal transients; and a microprocessor coupled to control said timing circuit and to control entry of said system into a calibration mode;

wherein during said calibration mode, said sample and hold circuit outputs a held signal having an amplitude proportional to an output of said MEAS-PD augmented by an output of said CAL-PD, and otherwise outputs a held signal having an amplitude proportional to said output of said MEAS-PD;

wherein a comparison between said held signal during calibration mode and otherwise closed provides data that enabling said microprocessor to correct said system for system drift;

wherein said held signal has an amplitude proportional to at least one said characteristic of said material.

16. The system of claim 15, wherein:

said LED is selected from a group consisting of (a) an LED emitting visible light, (b) an LED emitting infrared, and (c) an LED emitting laser light; and said material is filament-shaped and is selected from a group consisting of (a) synthetic yarn, (b) natural material yarn, and (c) yarn including synthetic and natural material.

17. The system of claim 15, wherein said drive signal has at least one characteristic selected from a group consisting of (a) said drive signal is a digital pulse train, (b) said drive signal has a duty cycle of about 50%, (c) said drive signal has a repetition rate ranging from about 10 KHz to about 100 KHz, and (d) said drive signal has a peak amplitude of about 5V.

18. An on-line method for real-time monitoring denier of a material, the method including the following steps:

(a) providing a collimated light source that outputs light synchronously in response to a periodic drive signal that has an active drive period when said light source emits light and that has an inactive drive period;

(b) disposing a planar array that includes at least a reference photodetector diode (REF-PD) and an identical measurement photodetector diode (MEAS-PD), said array being closely spaced apart from said source permitting said material to pass therebetween such that at least a fraction of light received by said MEAS-PD has passed through said material;

(c) optically feeding back, synchronously in phase and in frequency to said drive signal, an output of said REF-PD to alter amplitude of said periodic drive signal; and (d) sampling and holding an output of said MEAS-PD during a portion of said active drive period when the MEAS-PD output is substantially at steady-state.

19. An on-line system for real-time monitoring at least one characteristic of a material selected from a group consisting of (i) diameter and (ii) material defect, the system comprising:

a light source that emits collimated light synchronously in response to a drive signal;

a planar array that includes at least a first light detector and an identical second light detector, said array being closely spaced apart from said source permitting said material to pass therebetween such that at least a fraction of light received by said second light detector has passed through said material; and a synchronously optically coupled feedback circuit, having an input coupled to receive from one of said light detectors a signal synchronized in phase and frequency to said drive signal said feedback circuit outputting said drive signal to said light source.

20. The system of claim 19, wherein said first light detector is disposed to receive light emitted by said light source regardless of whether said material is present.

21. The system of claim 19, wherein said light source is selected from a group consisting of (a) a diode emitting visible light, (b) a diode emitting infrared, and (c) a laser diode.

22. The system of claim 19, wherein said material is a filament-like material selected from a group consisting of (a) synthetic yarn, (b) natural material yarn, (c) yarn including synthetic and natural material, and (d) wire.

23. The system of claim 19, wherein:
said second light detector is disposed to receive less light from said light source when said material is present;
said drive signal is a pulse train; and further including:
a first circuit so coupling a fraction of said drive signal to an output of said second light detector as to enhance dynamic range of said system.

24. The system of claim 23, further including:
a sample and hold circuit, having an input AC-coupled to receive a signal proportional to an output of said second light detector; and
a timing circuit that generates said drive signal, said driving signal having a duty cycle defining an active time region during which said light source emits light, and having an inactive time region;
said timing circuit also generating, in synchronism with a mid-time portion of said active time region, a pulse train controlling said sample and hold circuit such that said sample and hold samples and holds said signal proportional to an output of said second light source when said signal is substantially free of transients associated with said drive signal;
wherein an output of said sample and hold circuit has an analog amplitude proportional to at least one said optical transmissivity characteristic of said material.

25. The system of claim 24, further including:
an analog-to-digital converter having an input coupled to said output of said sample and hold circuit and having an output representing a digitized value of said sample and held output; and
a microprocessor, having an input coupled to receive said output of said analog-to-digital converter, and having an output coupled to control said timing circuit.

26. The system of claim 25, wherein said microprocessor further includes an interface coupled to communicate with a host computer able to download data to said microprocessor to control said system.

27. The system of claim 25, wherein said microprocessor further includes an interface coupled to a manufacturing system that is fabricating said material, wherein said system controls said manufacturing system.

28. The system of claim 24, wherein:
said array includes a third light detector identical to said second light detector, said third light detector disposed to receive less light from said light source when said material is present;
and further including:
a second circuit so coupling a fraction of said drive signal to an output of said third light detector so as to enhance dynamic range of said system;
timing circuit that generates said drive signal, said driving signal having a duty cycle defining an active time region during which said light source emits light, and having an inactive time region;
a calibration mode switch having a switch input coupled to said output of said third light detector and having a switch output coupled to said switch input when said system is in a calibration mode, said switch output floating when said system is not in said calibration mode; and
a sample and hold circuit, having an input AC-coupled an output of said second light detector and AC-coupled to said switch output;
said sample and hold circuit coupled to said signal proportional to an output of said second light detector when said system is not in said calibration mode, and coupled to said signal proportional to an output of said second light detector and coupled to a signal proportional to an output of said third light detector during said calibration mode;
wherein when said system is not in said calibration mode, a held signal at an output of said sample and hold switch has an analog amplitude proportional to at least one said optical transmissivity characteristic of said material; and
when said system is in said calibration mode, said held signal has an amplitude augmented by said signal proportional to an output of said third light detector;
wherein a comparison between said held signal when said calibration mode switch is open and when said calibration switch is closed provides information enabling said system to be corrected for system drift.

29. The system of claim 28, wherein:
said timing circuit also generates, in synchronism with a mid-time portion of said active time region, a pulse train controlling said sample and hold circuit such that said sample and hold samples and holds a signal that is substantially free of transients associated with said drive signal.

30. The system of claim 28, further including:
an analog-to-digital converter having an input coupled to said output of said sample and hold circuit and having an output representing a digitized value of said sample and held output; and
a microprocessor, having an input coupled to receive said output of said analog-to-digital converter, and having an output coupled to control said timing circuit.

31. The system of claim 28, further including:
a first AC-coupled amplifier coupled in series between said output of said second light detector and said input of said sample and hold circuit; and
a second AC-coupled amplifier, identical to said first amplifier, coupled in series between said output of said third light detector and said input of said sample and hold circuit.

32. The system of claim 19, wherein said drive signal has at least one characteristic selected form a group consisting of (a) said drive signal is a periodic pulse train, (b) said drive signal has a duty cycle of about 50%, (c) said drive signal has a repetition rate ranging from about 10 KHz to about 100 KHz, and (d) said drive signal has a peak amplitude of about 5V.

33. An on-line system for real-time monitoring at least one characteristic of a material selected from a group consisting of (i) diameter and (ii) material defect, the system comprising:
a light emitting diode (LED) that emits collimated light synchronously in response to a drive signal having a duty cycle defining an active time region during which said LED emits light, and having an inactive time region;
a planar array of photodetectors that includes a reference photodiode (REF-PD), an identical measurement photodiode (MEAS-PD) and an identical calibration photodiode (CAL-PD), said REF-PD being disposed to receive light emitted by said LED regardless of whether said material is present, said CAL-PD being disposed to receive less light from said LED when said material is present;

said array being closely spaced apart from said source permitting said material to pass therebetween such that at least a fraction of light received by said MEAS-PD has passed through said material;

a synchronously optically coupled feedback circuit, having an input coupled to receive an output signal, synchronized in phase and frequency to said drive signal, from said REF-PD and having an output providing said drive signal to said LED;

a sample and hold circuit, having an input AC-coupled to receive a signal proportional to said output of said MEAS-PD and AC-coupled, in a calibration mode, to receive a signal proportional to said output of said CAL-PD;

a timing circuit that generates said drive signal and further generates, in synchronism with a mid-time portion of said active time region, a pulse train controlling said sample and hold circuit such that a signal at the input of said sample and held is sampled and held at a time when said signal is substantially free of drive signal transients; and a microprocessor coupled to control said timing circuit and to control entry of said system into a calibration mode;

wherein during said calibration mode, said sample and hold circuit outputs a held signal having an amplitude proportional to an output of said MEAS-PD augmented by an output of said CAL-PD, and otherwise outputs a held signal having an amplitude proportional to said output of said MEAS-PD;

wherein a comparison between said held signal during calibration mode and otherwise closed provides data that enabling said microprocessor to correct said system for system drift;

wherein said held signal has an amplitude proportional to at least one said optical transmissivity characteristic of said material.

34. The system of claim 33, wherein:

said LED is selected from a group consisting of (a) an LED emitting visible light, (b) an LED emitting infrared, and (c) an LED emitting laser light; and said material is filament-shaped and is selected from a group consisting of (a) synthetic yarn, (b) natural material yarn, (c) yarn including synthetic and natural material, and (d) wire.

35. The system of claim 33, wherein said drive signal has at least one characteristic selected from a group consisting of (a) said drive signal is a digital pulse train, (b) said drive signal has a duty cycle of about 50%, (c) said drive signal has a repetition rate ranging from about 10 KHz to about 100 KHz, and (d) said drive signal has a peak amplitude of about 5V.

36. An on-line method for real-time monitoring at least one optical transmissivity characteristic of a material selected from a group consisting of (i) diameter and (ii) material defect, the method including the following steps:

(a) providing a collimated light source that outputs light synchronously in response to a periodic drive signal that has an active drive period when said light source emits light and that has an inactive drive period;

(b) disposing a planar array that includes at least a reference photodetector diode (REF-PD) and an identical measurement photodetector diode (MEAS-PD), said array being closely spaced apart from said source permitting said material to pass therebetween such that at least of fraction of light received by said MEAS-PD has passed through said material;

(c) DC-optically feeding back an output of said REF-PD, synchronously in phase and frequency to said drive signal, to alter amplitude of said periodic drive signal;

(d) sampling and holding an output of said MEAS-PD during a portion of said active drive period when the MEAS-PD output is substantially at steady-state;

wherein step (c) compensates monitoring against variations in light received from said light source by said REF-PD; and wherein at step (d), the sampled and held output of said MEAS-PD has a magnitude proportional to said at least one optical transmissivity characteristic.

* * * * *